United States Patent [19]

Mais et al.

[11] Patent Number: 5,105,036
[45] Date of Patent: Apr. 14, 1992

[54] PROCESS FOR RING-CHLORINATION OF AROMATIC HYDROCARBONS

[75] Inventors: Franz-Josef Mais, Duesseldorf; Helmut Fiege, Leverkusen, both of Fed. Rep. of Germany

[73] Assignee: Bayer Aktiengesellschaft, Leverkusen, Fed. Rep. of Germany

[21] Appl. No.: 651,715

[22] Filed: Feb. 6, 1991

[30] Foreign Application Priority Data

Feb. 16, 1990 [DE] Fed. Rep. of Germany ....... 4004821

[51] Int. Cl.$^5$ .................... C07C 17/12; C07C 25/00
[52] U.S. Cl. .................... 570/210; 570/190; 570/206; 570/207; 570/208; 570/209
[58] Field of Search ............... 570/190, 206, 207, 208, 570/209, 210

[56] References Cited

U.S. PATENT DOCUMENTS

| | | | |
|---|---|---|---|
| 4,748,287 | 5/1988 | Rohlk et al. | 570/209 |
| 4,851,596 | 7/1989 | Mais et al. | 570/209 |
| 4,925,994 | 5/1990 | Mais et al. | 570/210 |
| 4,990,707 | 2/1991 | Mais et al. | 570/210 |

*Primary Examiner*—Werren B. Lone
*Attorney, Agent, or Firm*—Sprung, Horn, Kramer & Woods

[57] ABSTRACT

Aromatic hydrocarbons monosubstituted by straight-chain or branched $C_1$–$C_{12}$-alkyl or by Chd 3–$C_8$-cycloalkyl can be chlorinated in the aromatic ring in the liquid phase in the presence of Friedel-Crafts catalysts if cyclic amidines which are oxy-sustituted on the exocyclic N atom are employed as co-catalysts. An increased proportion of the p-isomer is obtained in this reaction.

19 Claims, No Drawings

PROCESS FOR RING-CHLORINATION OF AROMATIC HYDROCARBONS

BACKGROUND OF THE INVENTION

1. Field of the Invention

The invention relates to a process for the ring-chlorination of aromatic hydrocarbons in the liquid phase in the presence of Friedel-Crafts catalysts and in the presence of co-catalysts.

2. Description of the Related Art

The reaction of aromatic hydrocarbons, such as toluene, with gaseous chlorine in the liquid phase to give ring-substituted chlorine derivatives, such as monochlorotoluene, is known (Ullmanns Enzyklopädie der Technischen Chemie (Ullmann's Encyclopaedia of Industrial Chemistry), 4th edition, Volume 9, page 499 et seq.). This chlorination is in general carried out in the presence of Friedel-Crafts catalysts, such as iron(III) chloride, antimony chlorides or aluminium chloride. The resulting chlorination product is usually a mixture of isomeric monochlorinated and polychlorinated compounds. If $FeCl_3$ is used, a mixture of monochlorotoluenes and dichlorotoluenes is obtained, for example, from toluene; in the monochlorotoluene fraction, the main product is o-chlorotoluene, alongside p-chlorotoluene and a small amount of m-chlorotoluene.

Since p-chloroalkylbenzenes, such as p-chlorotoluene, in particular are useful intermediate products, there has been no lack of attempts in the past to guide the chlorination so that the ratio of o- to p-chloroalkylbenzenes is reduced, that is to say attempts have been made to discover conditions which promote the formation of p-chloroalkylbenzenes.

It is known from U.S. Pat. No. 3,226,447 that an o/p ratio of 1.2 can be obtained in the chlorination of toluene by addition of sulphur compounds containing divalent sulphur to the Friedel-Crafts catalyst. The disadvantage of this process is the fact that this ratio, which is still not very favourable, is achieved only when antimony salts are used as the Friedel-Crafts catalysts. A further disadvantage is that according to Example 16 in that specification, the amounts of catalyst components required are very high, and in particular 1% by weight for each of the two catalytic additives. As the o/p ratio with a value of >1 shows, more o- than p-chlorotoluene is still formed in this process.

The chlorination of toluene with, for example $FeCl_3$ and $S_2Cl_2$ is likewise described in German Offenlegungsschrift 1,543,020 and U.S. Pat. No. 4,031,144. The resulting ratio of o/p=1.03-1.10 is still unsatisfactorily high.

The chlorination of toluene with Friedel-Crafts catalysts using thianthrenes or substituted thianthrenes is described in U.S. Pat. No. 4,031,147, U.S. Pat. No. 4,069,263, U.S. Pat. No. 4,069,264 and U.S. Pat. No. 4,250,122. The most favourable o/p ratios which can be achieved are about 0.7, but are obtained either only by using antimony salts or, in the case of the use of iron salts, only at very low reaction temperatures of about 0° C. Both these cases are decidedly unfavourable industrially. The co-catalytic action of thianthrenes is thus greatly impeded by traces of iron when antimony salts are used, and can be realized only with difficulty in industry. Furthermore, the reaction is so highly exothermic that removal of the heat at about 0° C. by cooling with brine becomes very expensive. The thianthrenes are furthermore already destroyed from ubiquitous traces of water under customary reaction conditions and thus lose their activity.

The chlorination of toluene in the presence of Lewis acids and phenoxathiines is furthermore known from U.S. Pat. No. 4,289,916, European Patent Specification 63,384 and European Patent Specification 173,222. The o/p ratio of 0.6 which can be achieved according to Example 1 of European Patent Specification 173,222 is again achieved only by the industrially extremely unfavourable use of antimony chloride and the high amount of 0.29% by weight of co-catalyst. If $FeCl_3$ is used instead of antimony chloride, an o/p ratio of 0.68 is obtained, but again only at the industrially extremely unfavourable low reaction temperature of 5° C. At an industrially advantageous reaction temperature of 50° C., the o/p ratio increases in the presence of $FeCl_3$ and the phenoxathiine derivative claimed in European Patent Specification 173,222 to 0.88; this can be seen from Comparison Example No. 50 from European Patent Specification 292,824. In the above U.S. Pat. No. 4,289,916 and European Patent Specification 63,384, a most favourable o/p ratio of about 0.8 is described. Here also, the o/p ratio can be lowered to 0.65 if antimony chlorides and a reaction temperature of 20° C., that is to say industrially unfavourable conditions, are used instead of $FeCl_3$. Phenoxathiines are also destroyed in the presence of traces of water.

Chlorination of toluene in the presence of Friedel-Crafts catalysts and N-substituted phenothiazines is known from European Patent Specification 126,669. The o/p ratio of 0.84 is also adversely high here.

The chlorination of toluene in the presence of certain zeolites is known from European Patent Specification 112,722, European Patent Specification 154,236 and European Patent Specification 248,931, an o/p ratio of about 0.3 being achieved with the addition of, for example, halogenocarboxylic acid halides as moderators. The considerable amounts of 5% by weight of zeolite and 1% by weight of moderators are a disadvantage of this process. As our own experiments have shown, this result must be paid for with the considerable disadvantage that very large amounts (up to 8% by weight) of benzyl chlorides occur in the resulting mixtures. However, the formation of benzyl chlorides interferes to a quite exceptional degree in the subsequent customary working up distillation.

The chlorination of alkylbenzenes having up to 12C atoms in the side chain in the presence of Friedel-Crafts catalysts and thiazepine derivatives as co-catalysts is known from European Patent Specification 292,824. A characteristic feature of the structure of the co-catalysts claimed in that specification is that 3 single bonds always originate from the nitrogen atom in the heterocyclic 7-membered ring. According to European Patent Specification 292,824, this N atom cannot enter into a double bond. The o/p ratio which can be achieved for toluene by this process is 0.64 in the best case (see Example 49 of European Patent Specification 292,824).

A process for the chlorination of alkylbenzenes having up to 12C atoms in the side chain in the presence of Friedel-Crafts catalysts and of thiazocin derivatives as co-catalysts is furthermore known from German Offenlegungsschrift 3,815,537 and German Offenlegungsschrift 3,824,068. Here also, a characteristic feature of the active co-catalyst structure is that only single bonds and no double bonds originate from the nitrogen atom of the heterocyclic 8-membered ring. The o/p ratio which can be achieved for toluene by this process is in the best case 0.78 (see Example 14 of German Offenlegungsschrift 3,815,537 or German Offenlegungsschrift 3,824,068).

SUMMARY OF THE INVENTION

A process has now been found for the ring-chlorination of aromatic hydrocarbons of the formula

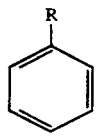
(I)

wherein
R denotes straight-chain or branched $C_1$-$C_{12}$-alkyl or $C_3$-$C_8$-cycloalkyl,
in the liquid phase in the presence of Friedel-Crafts catalysts and in the presence of co-catalysts, which is characterized in that the co-catalysts employed are cyclic amidines which are oxy-substituted on the exocyclic N atom, of the formula

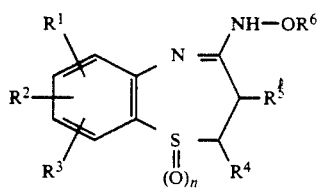
(II)

in which
$R^1$ and $R^2$ independently of one another denote hydrogen, cyano, halogen, carboxyl, alkoxycarbonyl, alkyl, aryl, alkoxy, aryloxy or acyl,
$R^3$ represents hydrogen, alkyl or chlorine, and furthermore can form a fused-on saturated, unsaturated or aromatic isocyclic or heterocyclic 5- to 8-membered ring with one of the radicals $R^1$ or $R^2$ in adjacent substitution and together with the substituted C atoms,
$R^4$ and $R^5$ independently of one another denote hydrogen, alkyl, aryl, halogen, alkoxy, aryloxy, acyl or acyloxy, or can form a saturated or unsaturated, isocyclic or heterocyclic 5- to 8-membered ring together with the substituted C atoms,
$R^6$ denotes hydrogen, alkyl, aryl or silyl which is substituted by alkyl or aryl and
n can assume the value zero or one.

DETAILED DESCRIPTION OF THE INVENTION

Fluorine, chlorine, bromine or iodine, preferably fluorine, chlorine or bromine and particularly preferably fluorine or chlorine, may be mentioned as halogen.

Alkyl radicals in the above substituents which may be mentioned are open-chain alkyl radicals having 1-16C atoms, preferably 1-4C atoms, and cyclic alkyl radicals having 5-8C atoms, preferably 5 or 6C atoms. These alkyl radicals can in turn be substituted by $C_1$-$C_4$-alkyl, preferably by methyl or ethyl, so that the series of branched alkyl radicals is also included. These alkyl radicals can furthermore be substituted by one or more fluorine, chlorine or bromine atoms. These alkyl radicals can furthermore be substituted by $C_1$-$C_4$-alkoxy, preferably by methoxy or ethoxy, so that the series of ethers is included. These alkyl radicals can furthermore be substituted by phenyl, naphthyl or biphenyl, so that the series of aralkyl radicals is included. Examples of such alkyl radicals are: methyl, ethyl, propyl, isopropyl, butyl, isobutyl, tert.-butyl, amyl, hexyl, octyl, decyl, dodecyl, hexadecyl, cyclopentyl, methylcyclopentyl, cyclohexyl, methylcyclohexyl, cycloheptyl, cyclooctyl, methoxymethyl, ethoxymethyl, benzyl, phenylethyl, chloromethyl, dichloromethyl, trichloromethyl and trifluoromethyl; examples of particularly important radicals are: methyl, ethyl, n-propyl, benzyl and trifluoromethyl.

The scope of meaning mentioned for alkyl radicals also applies on principle to alkoxy; radicals having 1-6C atoms, particularly preferably those having 1-4C atoms, such as methoxy, ethoxy, tert.-butoxy, cyclohexyloxy and trifluoromethoxy, are preferred.

Examples which may be mentioned of aryl radicals in the above substituents are phenyl, naphthyl and biphenyl, which can in turn be substituted by fluorine, chlorine, bromine, nitro, $C_1$-$C_4$-alkyl or $C_1$-$C_4$-alkoxy, for example phenyl, naphthyl, tolyl, anisyl, chlorophenyl and nitrophenyl; phenyl and chlorophenyl, for example, are particularly important.

Statements analogous to those made above for the alkoxy radicals apply in respect of the aryloxy radicals.

Acyl radicals in the above substituents have 1-8C atoms and are aliphatic, preferably having 2-4C atoms, or, with the required number of C atoms, are aromatic. They can in turn be substituted by the second substituents mentioned above for alkyl radicals and aryl radicals. Examples which may be mentioned are: acetyl, chloroacetyl, trichloroacetyl, trifluoroacetyl, benzoyl, chlorobenzoyl, chlorocarbonyl and formyl.

In the case where $R^3$ forms a ring with one of the radicals $R^1$ or $R^2$ and together with the substituted C atoms, this ring can be isocyclic and saturated, unsaturated or aromatic, or can also be heterocyclic as a result of a content of N, O and/or S atoms.

Such rings have 5-8, preferably 5 or 6, ring members and are fused onto the benzene ring shown in formula (II). Examples of such rings which may be mentioned are: benzo, naphthaleno, thieno, furano, pyrrolo, pyridino, cyclohexano, cyclopentano, oxolano and dioxolano, preferably benzo and cyclohexano.

In the case where $R^4$ and $R^5$ form a ring together with the substituted C atoms, this ring can be isocyclic and saturated or unsaturated or aromatic, or can also be heterocyclic as a result of a content of N, O and/or S atoms. Such rings likewise have 5-8, preferably 5 or 6, ring members and are fused onto the heterocyclic radical shown in formula (II). Examples which may be mentioned are those listed above, preferably cyclopentano, cyclohexano and dioxolano, particularly preferably cyclohexano.

The skeleton of the co-catalysts according to the invention is numbered as follows:

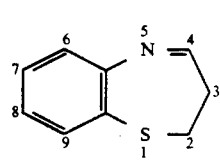
(IIa)

Since only the numbering is shown in formula (IIa), for clarity the possible substituents and the oxy-substituted N atom on the C atom in position 4 have been left out. The systems of the formula (II) which can be employed according to the invention as co-catalysts are characterized in that in these systems, in contrast to the systems of European Patent Specification 292,824, a double bond occurs between the N atom in position 5 of the heterocyclic 7-membered ring and the adjacent C atom in position 4 of the 7-membered ring, and in that furthermore this C atom in position 4 is substituted by an oxy-substituted N atom, that is to say by the grouping —N-H—O—$R^6$. They are thus cyclic amidines which are oxy-substituted on the exocyclic N atom and can be interpreted as derivatives of hydroxylamine.

The following list names examples of those co-catalysts which can be employed according to the invention, but without limiting the invention to these:

* N-(2,3-dihydro-1,5-benzothiazepin-4-yl)-hydroxylamine,
* N-(2-methyl-2,3-dihydro-1,5-benzothiazepin-4-yl)-hydroxylamine,
N-(2-ethyl-2,3-dihydro-1,5-benzothiazepin-4-yl)-hydroxylamine,
N-(2-propyl-2,3-dihydro-1,5-benzothiazepin-4-yl)-hydroxylamine,
* N-(3-methyl-2,3-dihydro-1,5-benzothiazepin-4-yl)-hydroxylamine,
* N-(2,3-dimethyl-2,3-dihydro-1,5-benzothiazepin-4-yl)-hydroxylamine,
N-(2-phenyl-2,3-dihydro-1,5-benzothiazepin-4-yl)-hydroxylamine,
N-(2-chloro-2,3-dihydro-1,5-benzothiazepin-4-yl)-hydroxylamine,
N-(2,3-dichloro-2,3-dihydro-1,5-benzothiazepin-4-yl)-hydroxylamine,
* N-(2-methoxy-2,3-dihydro-1,5-benzothiazepin-4-yl)-hydroxylamine,
N-(7-chloro-2,3-dihydro-1,5-benzothiazepin-4-yl)-hydroxylamine,
N-(6,8-dichloro-2,3-dihydro-1,5-benzothiazepin-4-yl)-hydroxylamine,
* N-(7-methyl-2,3-dihydro-1,5-benzothiazepin-4-yl)-hydroxylamine,
* N-(8-methyl-2,3-dihydro-1,5-benzothiazepin-4-yl)-hydroxylamine,
* N-(7,8-dimethyl-2,3-dihydro-1,5-benzothiazepin-4-yl)-hydroxylamine,
* N-(7,9-dimethyl-2,3-dihydro-1,5-benzothiazepin-4-yl)-hydroxylamine,
N-(7-trifluoromethyl-2,3-dihydro-1,5-benzothiazepin-4yl)-hydroxylamine,
* N-(8-benzyl-2,3-dihydro-1,5-benzothiazepin-4-yl)-hydroxylamine,
N-(8-acetyl-2,3-dihydro-1,5-benzothiazepin-4-yl)-hydroxylamine,
N-(8-trifluoroacetyl-2,3-dihydro-1,5-benzothiazepin-4-yl)-hydroxylamine,
N-(7-phenoxy-2,3-dihydro-1,5-benzothiazepin-4-yl)-hydroxylamine,
* N-(7-methoxy-2,3-dihydro-1,5-benzothiazepin-4-yl)-hydroxylamine,
* N-(8-methoxy-2,3-dihydro-1,5-benzothiazepin-4-yl)-hydroxylamine,
* N-(7,8-dimethoxy-2,3-dihydro-1,5-benzothiazepin-4-yl)-hydroxylamine,
* N-(7 9-dimethoxy -2,3-dihydro-1,5-benzothiazepin-4-yl)-hydroxylamine,
N-(7-phenyl-2,3-dihydro-1,5-benzothiazepin-4-yl)-hydroxylamine,
* N-(2,3-trimethylene-2,3-dihydro-1,5-benzothiazepin-4yl)-hydroxylamine,
* N-(2,3-tetramethylene-2,3-dihydro-1,5-benzothiazepin4-yl)-hydroxylamine,
* N-(7,8-dimethyl-2,3-tetramethylene-2,3-dihydro-1,5-benzothiazepin-4-yl)-hydroxylamine,
* N-(7,9-dimethyl-2,3-tetramethylene-2,3-dihydro-1,5-benzothiazepin-4-yl)-hydroxylamine,
* N-(7,9-dimethyl-6-chloro-2,3-tetramethylene-2,3-dihydro-1,5-benzothiazepin-4-yl)-hydroxylamine,
* N-(2,3,7,9-tetramethyl-2,3-dihydro-1,5-benzothiazepin-4-yl)-hydroxylamine,
* N-(3-methoxy-2,3-dihydro-1,5-benzothiazepin-4-yl)-hydroxylamine,
N-(3-acetyloxy-2,3-dihydro-1,5-benzothiazepin-4-yl)-hydroxylamine,
N-[3-acetyloxy-2-(methoxyphenyl)-2,3-dihydro-1,5-benzothiazepin-4-yl)-hydroxylamine,
N-(3-acetyloxy-2-phenyl-2,3-dihydro-1,5-benzothiazepin-4-yl)-hydroxylamine,
N-(1-oxo-2,3-dihydro-1,5-benzothiazepin-4-yl)-hydroxylamine,
N-(1-oxo-7,9-dimethyl-2,3-tetramethylene-2,3-dihydro-1,5-benzothiazepin-4-yl)-hydroxylamine,
N-(1-oxo-2,3,7,9-tetramethyl-2,3-dihydro-1,5-benzothiazepin-4-yl)-hydroxylamine,
* O-methyl-N-(2,3-dihydro-1,5-benzothiazepin-4-yl)-hydroxylamine,
O-ethyl-N-(2,3-dihydro-1,5-benzothiazepin-4-yl)-hydroxylamine,
O-benzyl-N-(2,3-dihydro-1,5-benzothiazepin-4-yl)-hydroxylamine,
* O-trimethylsilyl-N-(2,3-dihydro-1,5-benzothiazepin-4-yl)-hydroxylamine,
* O-trimethylsilyl-N-(7,9-dimethyl-2,3-tetramethylene-2,3-dihydro-1,5-benzothiazepin-4-yl)-hydroxylamine,
* O-methyl-N-(7,9-dimethyl-2,3-tetramethylene-2,3-dihydro-1,5-benzothiazepin-4-yl)-hydroxylamine;

the compounds identified with an * before the name are particularly important co-catalysts.

Preferred co-catalysts which can be employed according to the invention are generally cyclic amidines which are oxy-substituted on the exocyclic N atom, of the formula

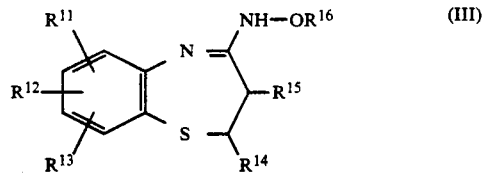

in which $R^{11}$ and $R^{12}$ independently of one another denote hydrogen, halogen, alkyl or alkoxy, $R^{13}$ represents hydrogen or alkyl, $R^{14}$ and $R^{15}$ independently of one another represent hydrogen, chlorine or alkyl, and furthermore can form a saturated isocyclic or heterocyclic 5- to 8-membered ring together with the substituted C atoms and $R^{16}$ denotes hydrogen, alkyl, aryl or trialkylsilyl.

Amongst the cyclic amidines of the formula (III), those in which the radicals $R^{22}$ and $R^{23}$, which independently of one another denote hydrogen or alkyl, occur instead of $R^{11}$ and $R^{12}$ are particularly preferred.

Amongst the cyclic amidines of the formula (III), those in which the radical $R^{13}$ denotes hydrogen are furthermore particularly preferred.

Amongst the cyclic amidines of the formula (III), those in which the radicals $R^{24}$ and $R^{25}$, which independently of one another denote hydrogen or alkyl and furthermore can form a saturated isocyclic 5- or 6-membered ring together with the substituted C atoms, are also furthermore particularly preferred.

The cyclic amidines which are oxy-substituted on the exocyclic N atom and can be employed according to the invention as co-catalysts can be prepared by processes which are known on principle, for example by reaction of 4-methylthio-2,3-dihydro-1,5-benzothiazepines with hydroxylamine or derivatives thereof in accordance with the following equation:

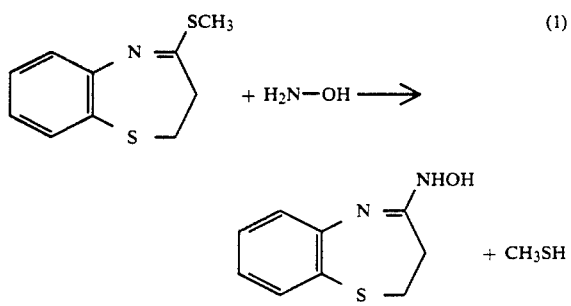
(1)

According to J. Heterocyc. Chem. 25 (1988), 1399, compounds of the type which can be employed according to the invention originate from this reaction (compare Embodiment Example 49). However, it is also possible to obtain such compounds by reaction of 2,3-dihydro-1,5-benzothiazepine-5(H)-4-thiones with hydroxylamine in accordance with the following equation.

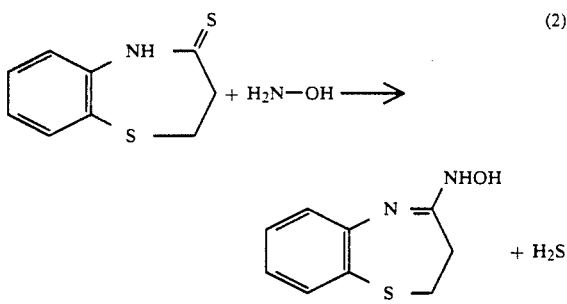
(2)

The product of the reaction according to equation (2) is identical to the product according to equation (1) (c.f. Embodiment Example 50).

It is furthermore conceivable that the compounds of the type which can be employed according to the invention are in the following tautomeric equilibrium:

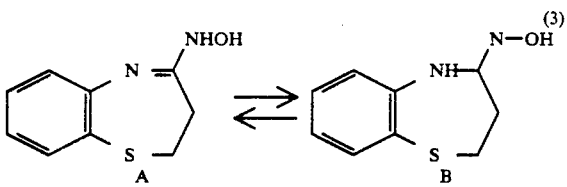
(3)

According to J. Heterocyc. Chem. 25 (1988), 1399, however, such compounds are in the A form.

Examples which may be mentioned of the aromatic hydrocarbons of the formula (I) which are to be chlorinated according to the invention in the ring are: toluene, ethylbenzene, propylbenzene, cumene, tert.-butylbenzene and phenyl-cyclohexane; the process according to the invention is particularly important for ring-chlorination of toluene.

The process according to the invention is carried out in the liquid phase, it being possible for the aromatic hydrocarbon to be employed in liquid (molten) form or if appropriate in dilution with an inert solvent. Suitable solvents are those which are not attacked by chlorine under the conditions of ring-chlorination and are known to the expert for this purpose, such as methylene chloride, chloroform, carbon tetrachloride and acetic acid. In the preferred form, the reaction is carried out without a solvent.

Chlorine is preferably used as the chlorinating agent for the process according to the invention. The chlorine can be passed in liquid or gaseous form into the reaction mixture. Gaseous chlorine is preferably employed.

However, it is also possible to use other chlorinating agents which, for example like sulphuryl chloride, donate chlorine under the reaction conditions.

The ring-chlorination to be carried out according to the invention can on principle be carried out at a temperature from the solidification point up to the boiling point of the reaction mixture. The reaction temperature is in general 0°–100° C., preferably 20°–80° C. and particularly preferably 40°–60° C.

The reaction pressure can be normal, reduced or increased and is on principle not critical. Normal pressure is preferred because of the inexpensive procedure. Increased pressure may be indicated, for example, if the reaction is to be carried out above the boiling point of a low-boiling solvent; in this case, for example, the reaction can be carried out under the autogenous pressure automatically established in the reaction mixture.

The degree of chlorination of the reaction mixture is preferably not substantially higher than 1, based on the aromatic hydrocarbon to be chlorinated. Higher degrees of chlorination are possible, but are not usually advantageous, since they lead to the formation of undesired polychlorinated products. The chlorine or a chlorine-donating substance is therefore employed, for example, in an amount of 0.8–1.1, preferably 0.8–1.0 mol per mol of the aromatic hydrocarbon.

The water content of the reaction mixture is in general not critical. It is preferable not to dry all the starting substances specifically but to employ them with the (low) water content with which they are normally present in the chemical industry. However, it is possible to dry individual substance or all the substances of the reaction mixture specifically. The water content of the starting substances should usually be not more than the saturation limits of the particular starting substances. Water contents in the chlorination mixture which are preferred according to the invention are those up to 250 ppm, particularly preferably up to 150 ppm and especially preferably up to 100 ppm.

Friedel-Crafts catalysts for the process according to the invention are all the known Friedel-Crafts catalysts, for example antimony chlorides, antimony oxychloride, aluminium chloride, iron(II) chloride, iron(III) chloride, tellurium chlorides, molybdenum chlorides, tungsten chlorides, titanium chlorides, zinc chloride, tin chlorides, boron trichloride and/or boron trifluoride. However, it is also possible for elements and element compounds which form a Friedel-Crafts catalyst (Lewis acid) during the chlorination, for example the elemental metals or semi-metals antimony, iron, lead, tin, zinc, molybdenum, tellurium and aluminium, or oxides, sulphides, carbonyls or salts thereof (for example carbonates or the like), to be employed. Examples which may be mentioned in this context are: antimony oxides, iron oxides, iron sulphides, lead sulphides, tin sulphides, zinc sulphides, iron carbonyls, molybdenum carbonyls and/or boron phosphate. Instead of the chlorides mentioned, it is also possible to employ the bromides, and if appropriate also the fluorides or iodides, of the elements mentioned. Preferred Friedel-Crafts catalysts are antimony chlorides, aluminium chloride, iron, iron oxides, iron sulphides, iron carbonyls and/or iron-(III) chloride. Iron(III) chloride is particularly preferred.

The amounts of the Friedel-Crafts catalyst or of a mixture of several of them can be varied within wide limits. A catalyst action is thus already detectable with an addition of 0.0005% by weight; on the other hand, 5% by weight or more of the Friedel-Crafts catalyst can also be added, but such high amounts in general offer no advantage and may bring difficulties during working up. The Friedel-Crafts catalyst is usually employed in an amount of 0.001–0.5% by weight, preferably 0.01–0.1% by weight. All the amounts data are based on the amount of aromatic hydrocarbon employed.

In addition to the abovementioned substances, the co-catalysts which can be employed according to the invention include all the substances which can form compounds or mixtures of compounds which fall under the formula (II) under the reaction conditions. All substances which can be formed by reaction of the abovementioned co-catalysts according to the invention with chlorine or hydrogen chloride under the reaction conditions of the chlorination can furthermore be employed. Examples which may be mentioned in this context are the hydrochlorides of the abovementioned co-catalysts.

It is furthermore possible for the co-catalysts to be employed in the process according to the invention with other elements or compounds which are not claimed as co-catalysts. The co-catalysts can be employed either individually or as a mixture of several of them. The amounts in which the co-catalysts according to the invention are employed can vary within wide limits. However, amounts below 0.0001% by weight are less advantageous, since the co-catalytic action then subsides. Amounts of 5% by weight or more of co-catalyst can even be added, but these high amounts in general offer no advantage and may cause working up problems. The co-catalysts according to the invention are therefore in general employed in an amount of 0.0001–0.5% by weight, preferably 0.0005–0.1% by weight and particularly preferably 0.0005–0.01% by weight, based on the aromatic hydrocarbon employed.

The molar ratio of the mixture of Friedel-Crafts catalyst(s) and co-catalyst(s) can be varied within wide limits in the process according to the invention. In general, it is advantageous for the co-catalyst not to be employed in too high an excess in comparison with the Friedel-Crafts catalyst. It is likewise in general more advantageous for the excess of Friedel-Crafts catalyst chosen also not to be too high. The molar ratio according to the invention of Friedel-Crafts catalyst to co-catalyst is 100:1–1:10, preferably 75:1–1:4 and particularly preferably 50:1–1:2.

Any desired sequence of addition of the individual components of the reaction mixture is possible for carrying out the process according to the invention in practice. The process can be carried out either continuously or discontinuously here. An example of an embodiment is the following:

The desired aromatic hydrocarbon, for example toluene, is initially introduced into the reaction vessel and brought to the desired temperature (for example 50° C.). The desired amounts of Friedel-Crafts catalyst(s) and co-catalyst(s) are then added in any desired sequence and gaseous chlorine is then passed in up to the desired degree of chlorination, whilst largely keeping the temperature constant. The mixture is then worked up in the customary manner by distillation.

Another example of an embodiment is the following:

A mixture of alkylbenzene with the desired contents of catalyst and co-catalyst is prepared and is brought to the desired reaction temperature. Chlorinating agent is then passed in until the desired degree of chlorination is reached. In this case too, working up can be carried out in the customary manner by distillation.

Another embodiment is the following:

A solution of catalyst and co-catalyst in the alkylbenzene is prepared and this is fed to a continuously operating chlorination apparatus. A chlorinating agent is passed in, also continuously, at a speed such that the desired degree of chlorination is reached. Here too, the reaction mixture continuously obtained can be worked up in the customary manner by distillation.

The possibility provided according to the invention of further shifting the isomer ratio in favour of the p-isomer in the ring-chlorination of alkylbenzenes is very surprising, because on the basis of the large number of thiazepines and thiazocins described in European Patent Specification 292,824 and in German Offenlegungsschrift 3,824,068 it was not to be expected that a derivative modified according to the invention again gives such a significant improvement, that is to say such a significant reduction in the o/p ratio.

The o/p ratio which can be achieved by the process according to the invention, for example for ring-chlorination of toluene, is about 0.55. This is the lowest o/p ratio which can be achieved to date for toluene using iron(III) chloride as the Friedel-Crafts catalyst at an average temperature of 40°–60° C. Such a reduction in the o/p ratio from 0.64 according to European Patent Specification 292,824 to about 0.55 means an increase in the p-content from a previous 61.0% to a present 64.5% in the mixture with a simultaneous decrease in the o-content from a previous 39.0% to a present 35.5%. This corresponds to a relative increase in the p-yield of 5.7%. This is a considerable advance, since according to European Patent Specification 63,384 (page 2, line 1–6 in that specification), increases in the p-isomer content of only 0.5% already denote a major advance and a great economic value.

The following examples are intended to illustrate the diversity of the process according to the invention, but without limiting it to these examples.

EXAMPLES

General implementation instructions 100 parts by weight of toluene were initially introduced into a reactor and the amounts of catalyst FeCl$_3$ and of co-catalyst shown in the table were added, while stirring. The mixture was heated to the stated temperature and the stated amount of chlorine (about 94 mol %) was uniformly passed in over a period of 5 hours, while stirring. The HCl waste gas formed was removed via a highly effective condenser. The chlorination mixture obtained was analyzed by gas chromatography, after calibration, so that the composition stated in the table represents a composition in per cent by weight.

The chlorination mixture can be broken down into the individual fractions, such as toluene, the isomeric monochlorotoluenes and the dichlorotoluene fraction, by industrially customary distillation.

The following table first contains those co-catalysts according to the invention in which $R^6$ in the formula (II) denotes hydrogen. The examples according to the invention ar each assigned two comparison examples, which are given either directly as an example in European Patent Specification 292,824 or fall within the claim of European Patent Specification 292,824. Example 1 is thus in comparison with Comparison Example 2 and Comparison Example 3, Example 4 is in comparison with Comparison Examples 5 and 6 and so on. These groups of three continue up to Example 34 and Comparison Examples 35 and 36.

If the particular co-catalyst according to the invention is compared with the two known comparison examples in the groups of three, the ability of the co-catalysts according to the invention to greatly reduce the o/p ratio again, that is to say to greatly increase the content of p-chlorotoluene in the chlorination mixture again, as desired, can be clearly and impressively seen.

Examples 37 to 40, which used co-catalysts in which $R^6$ in the formula (II) represents alkyl, phenyl-substituted alkyl or trialkylsilyl subsequently follow in the table. These examples were also carried out in accordance with the general instructions.

TABLE

| | Co-catalyst Formula | Co-catalyst Name | Temperature °C. | Amount of co-cat. in % by weight | Amount of FeCl₃ in % by weight | Amount of chlorine passed in, in mol% | Composition/chlorination mixture | | | | | |
|---|---|---|---|---|---|---|---|---|---|---|---|---|
| | | | | | | | Toluene % | o-Cl-toluene % | m-Cl-toluene % | p-Cl-toluene % | Dichloro-toluene % | o/p ratio |
| Example 1 | (structure with NH—OH) | N-(2,3-Dihydro-1,5-benzothiazepin-4-yl)-hydroxylamine | 50 | 0.0043 | 0.0175 | 94.0 | 3.79 | 37.70 | 0.65 | 57.03 | 0.83 | 0.66 |
| Comparison Example 2 | (structure with O) | 2,3-Dihydro-1,5-benzothiazepin-5H-4-one | 40 | 0.0040 | 0.0175 | 94.0 | 3.38 | 40.65 | 0.59 | 54.74 | 0.64 | 0.74 |
| Comparison Example 3 | (structure with S) | 2,3-Dihydro-1,5-benzothiazepine-5H-4-thione | 50 | 0.0046 | 0.0175 | 94.0 | 3.36 | 41.10 | 0.69 | 54.00 | 0.85 | 0.76 |
| Example 4 | (structure with NH—OH, CH₃) | N-(2-Methyl-2,3-dihydro-1,5-benzothiazepin-4-yl)-hydroxylamine | 50 | 0.0045 | 0.0175 | 94.0 | 2.94 | 37.88 | 0.63 | 57.61 | 0.94 | 0.66 |
| Comparison Example 5 | (structure with O, CH₃) | 2-Methyl-2,3-dihydro-1,5-benzothiazepin-5H-4-one | 50 | 0.0025 | 0.0175 | 94.0 | 4.13 | 39.93 | 0.79 | 53.99 | 1.16 | 0.74 |

TABLE-continued

| | Co-catalyst Formula | Co-catalyst Name | Temperature °C. | Amount of co-cat. in % by weight | Amount of FeCl₃ in % by weight | Amount of chlorine passed in, in mol% | Toluene % | o-Cl-toluene % | m-Cl-toluene % | p-Cl-toluene % | Dichloro-toluene % | o/p ratio |
|---|---|---|---|---|---|---|---|---|---|---|---|---|
| Comparison Example 6 | structure with N-H, S, CH₃ | 2-Methyl-2,3-dihydro-1,5-benzothiazepine-5H-4-thione | 50 | 0.0035 | 0.0175 | 94.8 | 2.45 | 40.84 | 0.75 | 54.23 | 1.73 | 0.75 |
| Example 7 | structure with NH—OH, C₃H₇ | N-(2-Propyl-2,3-Dihydro-1,5-benzothiazepin-4-yl)-hydroxylamine | 50 | 0.0051 | 0.0174 | 94.0 | 4.84 | 37.81 | 0.76 | 55.28 | 1.31 | 0.68 |
| Comparison Example 8 | structure with O, C₃H₇ | 2-Propyl-2,3-dihydro-1,5-benzothiazepin-5H-4-one | 55 | 0.0090 | 0.0175 | 94.0 | 4.02 | 40.22 | 0.73 | 54.17 | 0.86 | 0.74 |
| Comparison Example 9 | structure with N-H, S, C₃H₇ | 2-Propyl-2,3-dihydro-1,5-benzothiazepine-5H-4-thione | 50 | 0.0051 | 0.0174 | 94.0 | 4.92 | 38.86 | 0.94 | 53.93 | 1.35 | 0.72 |
| Example 10 | structure with NH—OH, CH₃, CH₃ | N-(2,3-Dimethyl-2,3-dihydro-1,5-benzothiazepin-4-yl)-hydroxylamine | 55 | 0.0048 | 0.0175 | 94.0 | 3.68 | 36.68 | 0.81 | 57.63 | 1.20 | 0.64 |

TABLE-continued

| | Co-catalyst Formula | Co-catalyst Name | Temperature °C. | Amount of co-cat. in % by weight | Amount of FeCl₃ in % by weight | Amount of chlorine passed in, in mol% | Toluene % | o-Cl-toluene % | m-Cl-toluene % | p-Cl-toluene % | Dichloro-toluene % | o/p ratio |
|---|---|---|---|---|---|---|---|---|---|---|---|---|
| Comparison Example 11 | (structure) | 2,3-Dimethyl-2,3-dihydro-1,5-benzothiazepin-5H-4-one | 55 | 0.0050 | 0.0175 | 94.2 | 3.00 | 39.48 | 0.85 | 55.41 | 1.26 | 0.71 |
| Comparison Example 12 | (structure) | 2,3-Dimethyl-2,3-dihydro-1,5-benzothiazepine-5H-4-thione | 55 | 0.0050 | 0.0175 | 94.0 | 3.41 | 40.09 | 0.80 | 54.52 | 1.18 | 0.73 |
| Example 13 | (structure) | N-(2,3-Tetramethylene-2,3-dihydro-1,5-benzothiazepin-4-yl)-hydroxylamine | 50 | 0.0053 | 0.0174 | 94.0 | 5.00 | 35.99 | 0.76 | 56.68 | 1.57 | 0.63 |
| Comparison Example 14 | (structure) | 2,3-Tetramethylene-2,3-dihydro-1,5-benzothiazepin-5H-4-one | 50 | 0.0050 | 0.0175 | 94.0 | 4.13 | 38.29 | 0.72 | 56.08 | 0.78 | 0.68 |
| Comparison Example 15 | (structure) | 2,3-Tetramethylene-2,3-dihydro-1,5-benzothiazepine,5H-4-thione | 50 | 0.0056 | 0.0174 | 94.2 | 3.13 | 38.39 | 0.80 | 56.64 | 1.04 | 0.68 |

TABLE-continued

| Co-catalyst Formula | Co-catalyst Name | Temperature °C. | Amount of co-cat. in % by weight | Amount of FeCl₃ in % by weight | Amount of chlorine passed in, in mol% | Toluene % | o-Cl-toluene % | m-Cl-toluene % | p-Cl-toluene % | Dichloro-toluene % | o/p ratio |
|---|---|---|---|---|---|---|---|---|---|---|---|
| Example 16  | N-(2-Phenyl-2,3-dihydro-1,5-benzothia-zepin-4-yl)-hydroxylamine | 52 | 0.0058 | 0.0174 | 94.0 | 5.70 | 45.10 | 0.82 | 45.39 | 2.99 | 0.99 |
| Comparison Example 17  | 2-Phenyl-2,3-dihydro-1,5-benzothiaze-pin-5H-4-one | 55 | 0.0050 | 0.0174 | 94.0 | 7.24 | 46.93 | 1.48 | 39.34 | 5.01 | 1.19 |
| Comparison Example 18 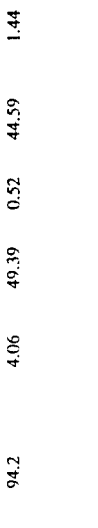 | 2-Phenyl-2,3-dihydro-1,5-benzothiazepine-5H-4-thione | 50 | 0.0061 | 0.0175 | 94.2 | 4.06 | 49.39 | 0.52 | 44.59 | 1.44 | 1.11 |
| Example 19  | N-(1-Oxo-2,3-dihydro-1,5-benzothiaze-pin-4-yl)-hydroxylamine | 50 | 0.0045 | 0.0174 | 94.0 | 4.25 | 37.90 | 0.62 | 56.77 | 0.46 | 0.67 |

TABLE-continued

| | Co-catalyst Formula | Co-catalyst Name | Temperature °C. | Amount of co-cat. in % by weight | Amount of FeCl₃ in % by weight | Amount of chlorine passed in, in mol% | Toluene % | Composition/chlorination mixture | | | | |
|---|---|---|---|---|---|---|---|---|---|---|---|---|
| | | | | | | | | o-Cl-toluene % | m-Cl-toluene % | p-Cl-toluene % | Dichloro-toluene % | o/p ratio |
| Comparison Example 20 | [structure] | 1-Oxo-2,3-dihydro-1,5-benzothiazepin-5H-4-one | 50 | 0.0050 | 0.0175 | 94.0 | 4.29 | 40.33 | 0.80 | 53.05 | 1.53 | 0.76 |
| Comparison Example 21 | [structure] | 1-Oxo-2,3-dihydro-1,5-benzothiazepine-5H-4-thione | 50 | 0.0046 | 0.0175 | 94.0 | 4.06 | 40.78 | 0.76 | 53.51 | 0.89 | 0.76 |
| Example 22 | [structure] | N-(6,8-Dichloro-2,3-dihydro-1,5-benzothiazepin-4-yl)-hydroxylamine | 50 | 0.0057 | 0.0175 | 94.0 | 5.07 | 41.38 | 1.27 | 49.85 | 2.43 | 0.83 |
| Comparison Example 23 | [structure] | 6,8-Dichloro-2,3-dihydro-1,5-benzothiazepin-5H-4-one | 50 | 0.0060 | 0.0175 | 94.0 | 4.37 | 44.04 | 1.11 | 48.93 | 1.55 | 0.90 |
| Comparison Example 24 | [structure] | 6,8-Dichloro-2,3-dihydro-1,5-benzothiazepine-5H-4-thione | 50 | 0.0057 | 0.0175 | 94.0 | 4.68 | 43.33 | 1.20 | 48.68 | 2.11 | 0.89 |
| Example 25 | [structure] | N-(7,8-Dimethyl-2,3-dihydro-1,5-benzothiazepin-4-yl)-hydroxylamine | 50 | 0.0048 | 0.0175 | 94.0 | 3.35 | 36.06 | 0.50 | 59.12 | 0.97 | 0.61 |

TABLE-continued

| Co-catalyst Formula | Co-catalyst Name | Temperature °C. | Amount of co-cat. in % by weight | Amount of FeCl₃ in % by weight | Amount of chlorine passed in, in mol% | Toluene % | Composition/chlorination mixture | | | | |
|---|---|---|---|---|---|---|---|---|---|---|---|
| | | | | | | | o-Cl-toluene % | m-Cl-toluene % | p-Cl-toluene % | Dichlorotoluene % | o/p ratio |
| Comparison Example 26: structure with N-H, C=O, S, CH₃, CH₃ | 7,8-Dimethyl-2,3-dihydro-1,5-benzothiazepine-5H-4-thione | 50 | 0.0047 | 0.0175 | 94.0 | 3.03 | 38.97 | 0.59 | 56.60 | 0.81 | 0.69 |
| Comparison Example 27: structure with N-H, C=S, S, CH₃, CH₃ | 7,8-Dimethyl-2,3-dihydro-1,5-benzothiazepine-5H-4-thione | 50 | 0.0048 | 0.0175 | 94.0 | 3.32 | 39.63 | 0.64 | 55.83 | 0.58 | 0.71 |
| Example 28: structure with N-OH, S, CH₃, CH₃ | N-(7,9-Dimethyl-2,3-dihydro-1,5-benzothiazepin-4-yl)-hydroxylamine | 50 | 0.0047 | 0.0174 | 94.0 | 4.01 | 36.15 | 0.57 | 58.05 | 1.22 | 0.62 |
| Comparison Example 29: structure with N-H, C=O, S, CH₃, CH₃ | 7,9-Dimethyl-2,3-dihydro-1,5-benzothiazepin-5H-4-one | 50 | 0.0047 | 0.0175 | 94.0 | 2.84 | 39.87 | 0.61 | 56.04 | 0.64 | 0.71 |
| Comparison Example 30: structure with N-H, C=S, S, CH₃, CH₃ | 7,9-Dimethyl-2,3-dihydro-1,5-benzothiazepine-5H-4-thione | 50 | 0.0047 | 0.0175 | 94.0 | 3.75 | 38.46 | 0.70 | 55.46 | 1.63 | 0.69 |

| | | | | | | | Composition/chlorination mixture | | | | | |
|---|---|---|---|---|---|---|---|---|---|---|---|---|
| | Co-catalyst Formula | Co-catalyst Name | Temperature °C. | Amount of co-cat. in % by weight | Amount of FeCl₃ in % by weight | Amount of chlorine passed in, in mol% | Toluene % | o-Cl-toluene % | m-Cl-toluene % | p-Cl-toluene % | Dichloro-toluene % | o/p ratio |
| Example 31 | [structure with NH—OH] | N-(2,3,7,9-Tetramethyl-2,3-dihydro-1,5-benzo-thiazepin-4-yl)-hydroxyl-amine | 50 | 0.0054 | 0.0175 | 94.2 | 3.59 | 35.66 | 0.65 | 59.12 | 0.98 | 0.60 |
| Comparison Example 32 | [structure with O] | 2,3,7,9-Tetramethyl-2,3-dihydro-1,5-benzothiaze-pine-5H-4-one | 55 | 0.0053 | 0.0175 | 94.0 | 3.14 | 38.29 | 0.68 | 57.10 | 0.79 | 0.67 |
| Comparison Example 33 | [structure with S] | 2,3,7,9-Tetramethyl-2,3-dihydro-1,5-benzothiaze-pine-5H-4-thione | 50 | 0.0054 | 0.0175 | 94.0 | 4.77 | 38.06 | 0.90 | 54.25 | 2.02 | 0.70 |
| Example 34 | [structure with NH—OH and cyclohexyl] | N-(7,9-Dimethyl-2,3-tetramethylene-2,3-dihydro-1,5-benzothiaze-pin-4-yl)-hydroxylamine | 50 | 0.0059 | 0.0175 | 94.0 | 4.00 | 33.61 | 0.56 | 61.02 | 0.81 | 0.55 |
| Comparison Example 35 | [structure with O and cyclohexyl] | 7,9-Dimethyl-2,3-tetramethylene-2,3-dihydro-1,5-benzothiazepin-5H-4-one | 55 | 0.0057 | 0.0175 | 94.0 | 3.37 | 37.33 | 0.65 | 57.89 | 0.76 | 0.64 |

TABLE-continued

| | Co-catalyst Formula | Co-catalyst Name | Temperature °C. | Amount of co-cat. in % by weight | Amount of FeCl3 in % by weight | Amount of chlorine passed in, in mol% | Toluene % | Composition/chlorination mixture | | | | o/p ratio |
|---|---|---|---|---|---|---|---|---|---|---|---|---|
| | | | | | | | | o-Cl-toluene % | m-Cl-toluene % | p-Cl-toluene % | Dichloro-toluene % | |
| Comparison Example 36 | | 7,9-Dimethyl-2,3-tetra-methylene-2,3-dihydro-1,5-benzothiazepine-5H-4-thione | 50 | 0.0059 | 0.0175 | 94.0 | 3.81 | 37.18 | 0.77 | 57.41 | 0.83 | 0.65 |
| Example 37 | | O-Methyl-N-(2,3-dihydro-1,5-benzothiazepin-4-yl)-hydroxyl-amine | 50 | 0.0045 | 0.0175 | 94.0 | 3.52 | 38.08 | 0.67 | 56.37 | 1.36 | 0.67 |
| Example 38 | | O-Ethyl-N-(2,3-dihydro-1,5-benzo-thiazepin-4-yl)-hydroxyl-amine | 50 | 0.048 | 0.0175 | 94.0 | 4.59 | 37.69 | 0.61 | 56.24 | 0.87 | 0.67 |
| Example 39 | | O-Benzyl-N-(2,3-dihydro-1,5-benzo-thiazepin-4-yl)-hydroxyl-amine | 50 | 0.061 | 0.0175 | 94.0 | 4.53 | 38.14 | 0.63 | 55.74 | 0.96 | 0.68 |
| Example 40 | | O-Trimethylsilyl-N-(2,3-dihydro-1,5-benzothia-zepin-4-yl)-hydroxylamine | 50 | 0.0072 | 0.00174 | 94.0 | 3.53 | 38.11 | 0.61 | 56.97 | 0.88 | 0.67 |

The following examples and comparison examples illustrate the invention for ring-chlorination of other alkylbenzenes according to formula (I).

EXAMPLE 41

(Ring-chlorination according to the invention of ethylbenzene)

0.0175 part by weight of FeCl₃ and 0.045 part by weight of the co-catalyst of the formula

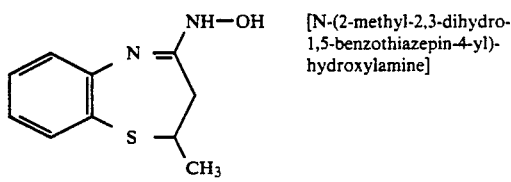
[N-(2-methyl-2,3-dihydro-1,5-benzothiazepin-4-yl)-hydroxylamine]

were added to 100 parts by weight of ethylbenzene at room temperature and the mixture was heated to 50° C. 94.0 mol % of Cl₂ were uniformly passed in over a period of 5 hours analogously to the general instructions. The chlorination mixture was analyzed by gas chromatography. The composition of the chlorination mixture was as follows: 6.75% by weight of ethylbenzene, 29.60% by weight of ortho-chloroethylbenzene, 0.71% by weight of meta-chloroethylbenzene, 62.21% by weight of para-chloroethylbenzene and 0.73% by weight of dichloroethylbenzenes. The o/p ratio is thus 0.47.

COMPARISON EXAMPLE 42

(Ring-chlorination of ethylbenzene according to European Patent Specification 292,824)

The process of Example 41 was repeated, but instead of the co-catalyst in that example, 0.0050 part by weight of the co-catalyst of the formula

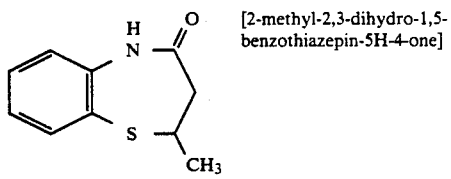
[2-methyl-2,3-dihydro-1,5-benzothiazepin-5H-4-one]

was added. The composition of the chlorination mixture was as follows:

4.22% by weight of ethylbenzene, 33.12% by weight of ortho-chloroethylbenzene, 0.89% by weight of meta-chloroethylbenzene, 60.76% by weight of para-chloroethylbenzene and 1.01% by weight of dichloroethylbenzenes. The o/p ratio is thus 0.54.

EXAMPLE 43

(Ring-chlorination according to the invention of isopropylbenzene)

The process of Example 41 was repeated, but instead of ethylbenzene 100 parts by weight of isopropylbenzene and instead of the co-catalyst in that example 0.048 part by weight of the co-catalyst of the formula

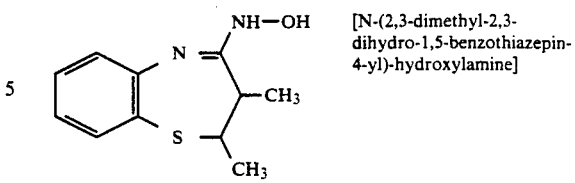
[N-(2,3-dimethyl-2,3-dihydro-1,5-benzothiazepin-4-yl)-hydroxylamine]

were used. The composition of the chlorination mixture was as follows: 6.73% by weight of isopropylbenzene, 8.37% by weight of ortho-chloroisopropylbenzene, 1.09% by weight of meta-chloroisopropylbenzene, 73.40% by weight of para-chloroisopropylbenzene and 0.41% by weight of dichloroisopropylbenzenes. The o/p ratio is thus 0.25.

COMPARISON EXAMPLE 44

(Ring-chlorination of isopropylbenzene according to European Patent Specification 292,284)

The process of Example 41 was repeated, but instead of ethylbenzene 100 parts by weight of isopropylbenzene and instead of the co-catalyst in that example 0.005 part by weight of the co-catalyst of the formula

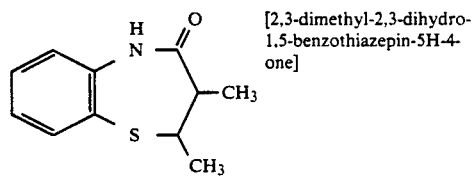
[2,3-dimethyl-2,3-dihydro-1,5-benzothiazepin-5H-4-one]

were used. The composition of the chlorination mixture was as follows: 3.38% by weight of isopropylbenzene, 21.17% by weight of ortho-chloroisopropylbenzene, 1.38% by weight of meta-chloroisopropylbenzene, 73.02% by weight of para-chloroisopropylbenzene and 1.04% by weight of dichloroisopropylbenzenes. The o/p ratio is thus 0.29.

EXAMPLE 45

(Ring-chlorination according to the invention of t.-butyl-benzene)

The process of Example 41 was repeated, but instead of ethylbenzene 100 parts by weight of t.-butyl-benzene and instead of the co-catalyst in that example 0.0042 part by weight of the co-catalyst of the formula

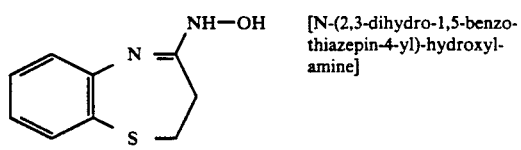
[N-(2,3-dihydro-1,5-benzothiazepin-4-yl)-hydroxylamine]

were used. The composition of the chlorination mixture was as follows: 7.61% by weight of t.-butylbenzene, 10.63% by weight of ortho-chloro-t.-butylbenzene, 0.89% by weight of meta-chloro-t.-butylbenzene, 79.68% by weight of para-chloro-t.-butylbenzene and 1.19% by weight of dichloro-t.-butylbenzenes. The o/p ratio is thus 0.13.

COMPARISON EXAMPLE 46

(Ring-chlorination of t.-butylbenzene according to European Patent Specification 292,824)

The process of Example 41 was repeated, but instead of ethylbenzene 100 parts by weight of t.-butyl-benzene and instead of the co-catalyst in that example 0.0045 part by weight of the co-catalyst of the formula

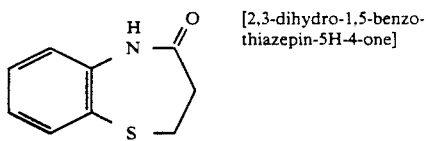
[2,3-dihydro-1,5-benzo-thiazepin-5H-4-one]

were used. The composition of the chlorination mixture was as follows:

8.91% by weight of t.-butylbenzene, 12.91% by weight of ortho-chloro-t.-butylbenzene, 0.95% by weight of metachloro-t.-butylbenzene, 75.94% by weight of para-chloro-t.-butylbenzene and 1.29% by weight of dichloro-t.-butylbenzenes. The o/p ratio is thus 0.17.

EXAMPLE 47

(Ring-chlorination of chlorohexylbenzene)

The process of Example 41 was repeated, but instead of ethylbenzene 100 parts by weight of cyclohexylbenzene and instead of the co-catalyst in that example 0.0046 part by weight of the co-catalyst of the formula

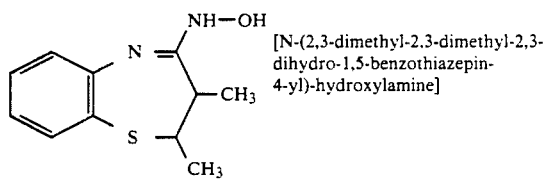
[N-(2,3-dimethyl-2,3-dimethyl-2,3-dihydro-1,5-benzothiazepin-4-yl)-hydroxylamine]

were used. The composition of the chlorination mixture was as follows:

5.09% by weight of cyclohexylbenzene, 15.51% by weight of ortho-chlorocyclohexylbenzene, 0.70% by weight of meta-chlorocyclohexylbenzene, 76.76% by weight of para-chlorocyclohexylbenzene and 1.94% by weight of dichloro-cyclohexylbenzenes. The o/p ratio is thus 0.20.

COMPARISON EXAMPLE 48

(Ring-chlorination of cyclohexylbenzene according to European Patent Specification 292,824)

The process of Example 41 was repeated, but instead of ethylbenzene 100 parts by weight of cyclohexylbenzene and instead of the co-catalyst in that example 0.0045 part by weight of the co-catalyst of the formula

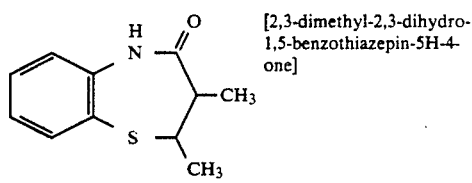
[2,3-dimethyl-2,3-dihydro-1,5-benzothiazepin-5H-4-one]

were used. The composition of the chlorination mixture was as follows:

2.63% by weight of cyclohexylbenzene, 19.06% by weight of ortho-chloro-cyclohexylbenzene, 1.09% by weight of meta-chloro-cyclohexylbenzene, 76.24% by weight of parachloro-cyclohexylbenzene and 0.98% by weight of dichloro-cyclohexylbenzenes. The o/p ratio is thus 0.25.

The Examples and Comparison Examples 41 to 48 clearly show that the co-catalysts according to the invention also give a low o/p value (that is to say a higher content of the p-chloroalkylbenzene isomer) than the co-catalysts known, for example, from European Patent Specification 292,284 in the ring-chlorination of other alkylbenzenes of the formula (I).

The preparation of co-catalysts of the formula (II) is described below by the example of the compound N-(2,3-dihydro-1,5-benzothiazepin-4-yl)-hydroxylamine.

EXAMPLE 49

(According to J. Heterocycl. Chem 25, (1988) 1399)

2.40 g (34.53 mmol) of hydroxylammonium chloride and 3.50 g (34.65 mmol) of triethylamine were added to a solution of 5.25 g (25.12 mmol) of 4-methylthio-2,3-dihydro-1,5-benzothiazepine in 20 ml of absolute ethanol and the mixture was stirred under reflux for 20 hours (−78° C.). The mixture was then evaporated to dryness and the residue was recrystallized from 70% strength ethanol (remainder: H$_2$O) and dried thoroughly.

Yield: 2.85 g (58.5% of the theoretical yield)
Melting point: 194°-196° C. (literature 194°-195° C.)

The product showed only one spot on a thin layer chromatography plate (silica gel)/mobile phase: methylene dichloride.

EXAMPLE 50

13.90 g (200.00 mmol) of hydroxylammonium chloride and 20.20 g (200.00 mmol) of triethylamine were added to a solution of 19.50 g (100.00 mmol) of 2,3-dihydro-1,5-benzothiazepine-5H-4-thione in 200 ml of absolute ethanol. The mixture was heated under reflux for 6 hours and then evaporated to dryness. The residue was extracted by stirring with 0.5 l of water and 0.5 l of methylene chloride and the methylene chloride phase was separated off, dried with MgSO$_4$ and evaporated again. This second residue was recrystallized from 70% strength ethanol (remainder H$_2$O) and dried thoroughly.

Yield: 16.50 g (85.0% of the theoretical yield)
Melting point: 194°-196° C.

According to the melting point and mixed melting point and the thin layer chromatography comparison analysis, the product was identical to that from Example 49.

What is claimed is:

1. A process for the ring-chlorination of an aromatic hydrocarbon of the formula

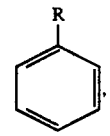

wherein
denotes straight-chain or branched C$_1$-C$_{12}$-alkyl or C$_3$-C$_8$-cycloalkyl,
in the liquid phase in the presence of a chlorinating agent selected from the group consisting of chlorine and sulfuryl chloride and in the presence of Friedel-Crafts catalyst selected from the group consisting of antimony chlorides, antimony oxychlorides, aluminum chloride, iron(II)-chloride, iron(III)-chloride, tellurium chlorides, molybdenum chlorides, tungsten chlorides, titanium chlorides, zinc chloride, tin chlorides, boron trichloride, boron trifluoride and the elements or other compounds of elements which form a Friedel-Crafts catalyst, and in the presence of a co-catalyst, wherein the co-catalyst employed is a cyclic amidine which is oxy-substituted on the exocyclic N atom, of the formula

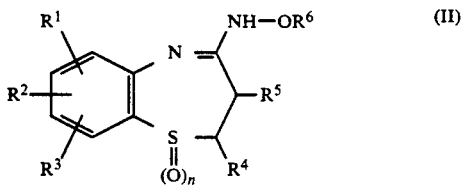

in which

R$^1$ and R$^2$ independently of one another denote hydrogen, cyano, halogen, carboxyl, alkoxycarbonyl, alkyl, aryl, alkoxy, aryloxy or acyl, R$^3$ represents hydrogen, alkyl or chlorine, and furthermore can form a fused-on saturated, unsaturated or aromatic isocyclic or heterocyclic 5- to 8-membered ring with one of the radicals R$^1$ or R$^2$ in adjacent substitution and together with the substituted C atoms, R$^4$ and R$^5$ independently of one another denote hydrogen, alkyl, aryl, halogen, alkoxy, aryloxy, acyl or acyloxy, or can form a saturated or unsaturated, isocyclic or heterocyclic 5- to 8-membered ring together with the substituted C atoms, R$^6$ denotes hydrogen, alkyl, aryl or silyl which is substituted by alkyl or aryl and n can assume the value zero or one.

2. The process of claim 1, wherein a cyclic amidine of the formula

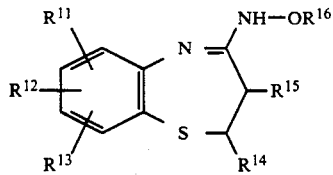

in which

R$^{11}$ and R$^{12}$ independently of one another denote hydrogen, halogen, alkyl or alkoxy, R$^{13}$ represents hydrogen or alkyl, R$^{14}$ and R$^{15}$ independently of one another represent hydrogen, chlorine or alky, and furthermore can form a saturated isocyclic or heterocyclic 5- to 8-membered ring together with the substituted C atoms and R$^{16}$ denotes hydrogen, alkyl, aryl or trialkylsilyl, is employed.

3. The process of claim 2, wherein the radicals R$^{22}$ and R$^{23}$, which independently of one another denote hydrogen or alky, occur instead of R$^{11}$ and R$^{12}$, 4. The process of claim 2, wherein the radical R$^{13}$ denotes hydrogen.

5. The process of claim 2, wherein the radicals R$^{24}$ and R$^{25}$, which independently of one another denote hydrogen or alkyl and furthermore can form a saturated isocyclic 5- or 6-membered ring together with the substituted C atoms, occur instead of R$^{14}$ and R$^{15}$.

6. The process of claim 1, wherein the ring-chlorination is carried out at a temperature from the solidification Point up to the boiling point of the reaction mixture.

7. The process of claim 6, wherein the ring-chlorination is carried out at a temperature from 0°-100° C.

8. The process of claim 7, wherein the ring-chlorination is carried out at a temperature from 20°-80° C.

9. The process of claim 8, wherein the ring-chlorination is carried out at a temperature from 40°-60° C.

10. The process of claim 1, wherein 0.8-1.1 mol of chlorine or sulfuryl chloride are employed per mol of the aromatic hydrocarbon.

11. The process of claim 10, wherein 0.8-1.0 mol of chlorine or sulfuryl chloride are employed per mol of the aromatic hydrocarbon.

12. The process of claim 1, wherein the amount of Friedel-Crafts catalyst employed is 0.001-0.5% by weight, based on the aromatic hydrocarbon employed.

13. The process of claim 12, wherein the amount of Friedel-Crafts catalyst is 0.01-0.1% by weight based on the aromatic hydrocarbon employed.

14. The process of claim 1, wherein the amount of co-catalyst employed is 0.0001-0.5% by weight, based on the aromatic hydrocarbon employed.

15. The process of claim 14, wherein the amount of co-catalyst employed is 0.0005-0.1% by weight based on the aromatic hydrocarbon employed.

16. The process of claim 15, wherein the amount of co-catalyst employed is 0.0005-0.01% by weight, based on the aromatic hydrocarbon employed.

17. The process of claim 1, wherein the molar ratio of Friedel-Crafts catalyst to co-catalyst is 100:1-1:10.

18. The process of claim 17, wherein the molar ratio of Friedel-Crafts catalyst to co-catalyst is 75:1-1:4.

19. The process of claim 18, wherein the molar ratio of Friedel-Crafts catalyst to co-catalyst is 50:1—1:2.

* * * * *

UNITED STATES PATENT AND TRADEMARK OFFICE
CERTIFICATE OF CORRECTION

PATENT NO. : 5,105,036

DATED : April 14, 1992

INVENTOR(S) : Mais et al.

It is certified that error appears in the above-identified patent and that said Letters Patent is hereby corrected as shown below:

Title Page      ABSTRACT: Line 2 delete " Chd 3-$C_8$- " and substitute -- $C_3$-$C_8$- --

Col. 32, line 62    Before " denotes " insert -- R --

Signed and Sealed this

Second Day of November, 1993

Attest:

BRUCE LEHMAN

Attesting Officer    Commissioner of Patents and Trademarks